United States Patent
Carrier

(10) Patent No.: US 8,703,487 B2
(45) Date of Patent: Apr. 22, 2014

(54) COMPOSITIONS AND METHODS FOR MAKING AND USING BONE MARROW MESENCHYMAL STEM CELLS AND ERYTHROID PROGENITOR CELLS

(75) Inventor: Ewa Carrier, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/512,872

(22) PCT Filed: Nov. 30, 2010

(86) PCT No.: PCT/US2010/058384
§ 371 (c)(1),
(2), (4) Date: Sep. 18, 2012

(87) PCT Pub. No.: WO2011/068792
PCT Pub. Date: Jun. 9, 2011

(65) Prior Publication Data
US 2013/0052728 A1 Feb. 28, 2013

Related U.S. Application Data

(60) Provisional application No. 61/265,486, filed on Dec. 1, 2009.

(51) Int. Cl.
*C12N 5/07* (2010.01)
*C12N 5/071* (2010.01)

(52) U.S. Cl.
USPC .......................... 435/347; 435/366

(58) Field of Classification Search
None
See application file for complete search history.

(56) References Cited

U.S. PATENT DOCUMENTS

| 5,914,268 | A | 6/1999 | Keller et al. | |
| 2007/0128722 | A1 | 6/2007 | Lin et al. | |
| 2009/0274770 | A1* | 11/2009 | Gammelsaeter et al. | 424/581 |
| 2010/0158880 | A1* | 6/2010 | Seyda et al. | 424/93.21 |
| 2010/0279403 | A1* | 11/2010 | Rajesh et al. | 435/366 |

FOREIGN PATENT DOCUMENTS

| WO | 2007123363 A1 | 11/2007 |
| WO | 2007136157 A1 | 11/2007 |
| WO | 2009137629 A2 | 11/2009 |

OTHER PUBLICATIONS

Ren, H., Cao, Y., Zhao,k Q., Li, J., Zhou, C., Liao, L., Jia, M., Zhao, Q., Cai, H., Chao Han, Z., Yang, R., Che, G., Chunhua Zao, R. "Proliferation and differentiation of bone marrow stromal cells under hypoxic conditions", Biochemical and Biophysical Research Communications 2006, vol. 347, pp. 12-21.*
Volkmer, E., Kallukalam, B.C., Maertz, J., Otto, S., Drosse, I., Polzer, H., Bocker, W., Stengele, M., Docheva, D., Mutschler, W., and Schieker, M. "Hypoxic Preconditioning of Human Mesenchymal Stem Cells Overcomes Hypoxia-Induced Inhibition of Osteogenic Differentiation", Tissue Engineering: Part A 2010 (online: Sep. 2009), vol. 16, pp. 153-164.*
Beom, Kim Seung, International Search Report, WO 2011/068792A3, PCT Application No. PCT/US2010/058384, Korean Patent Office, Aug. 4, 2011.
Hu, Xinyang et al., Transplantation of hypoxia-preconditioned mesenchymal stem cells improves infarcted heart function via enhanced survival of implanted cells and angiogenesis, The Journal of Thoracic and Cardiovascular Surgery, vol. 135, No. 4, pp. 799-808, Oct. 2008.
Lindner, Nora, International Preliminary Report on Patentability and Written Opinion, PCT/US2010/058384, The International Bureau of WIPO, Jun. 5, 2012.
Rosova, Ivana et al., "Hypoxic Preconditioning Results in Increased Motility and Improved Therapeutic Potential of Human Mesenchymal Stem Cells," Stem Cells, 2008, 26:2173-2182.
Shingo, Tetsuro et al., Erythropoietin Regulates the In Vitro and In Vivo Production of Neuronal Porgenitors by Mammalian Forebrain Neural Stem Cells, The Journal of Neuroscience, Dec. 15, 2011, 21(24):9733-9743.
Ueno, M. et al., "Enhanced erythropoietin secretion in hepatoblastoma cells in response to hypoxia," Am J. Physiol. Cell Physiol., 257:C743-C749, 1989.
Zwezdaryk, Kevin J. et al., "Erythropoietin, a hypoxia-regulated factor, elicits a pro-angiogenic program in human mesenchymal stem cells," Experimental Hematology 35 (2007) 640-652.

* cited by examiner

*Primary Examiner* — Allison Ford
*Assistant Examiner* — Michelle F Paguio Frising
(74) *Attorney, Agent, or Firm* — Gregory P. Einhorn; Gavrilovich, Dodd & Lindsey LLP

(57) ABSTRACT

The invention provides compositions for making erythroid progenitor cells that comprise in vitro-activated bone marrow mesenchymal stem cells and embryoid bodies (EBs) or pluripotent stem cells, and methods for making and using them, including ameliorating (e.g., preventing or treating) anemia and/or stimulating erythropoiesis. In one embodiment, the invention provides methods of increasing propensity of committed stem cell differentiation towards the erythroid lineage.

18 Claims, 1 Drawing Sheet

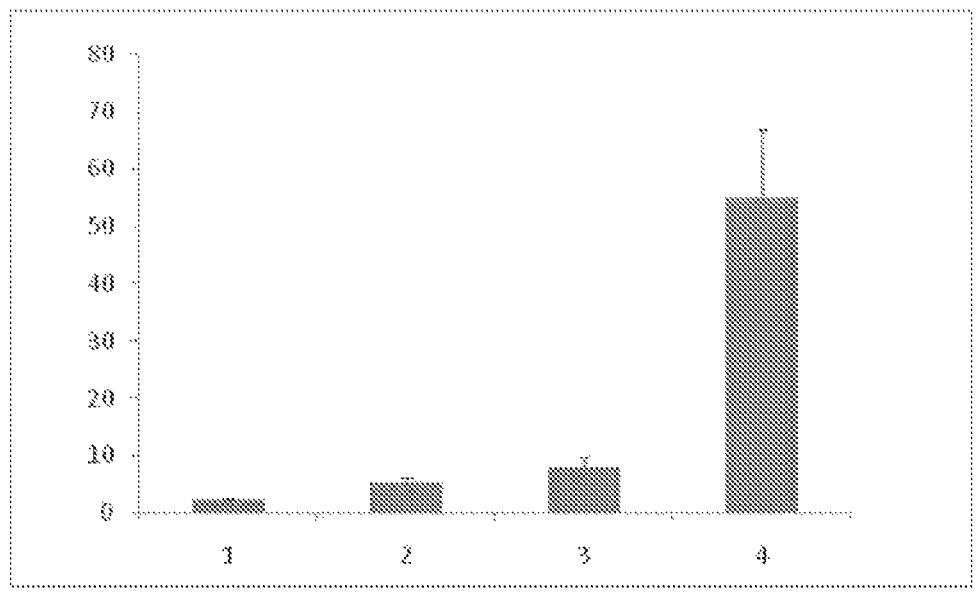

US 8,703,487 B2

COMPOSITIONS AND METHODS FOR MAKING AND USING BONE MARROW MESENCHYMAL STEM CELLS AND ERYTHROID PROGENITOR CELLS

CROSS-REFERENCE TO RELATED APPLICATIONS

This United States utility patent application is the §371 national phase of PCT international patent application no. PCT/US2010/058384 having an international filing date of Nov. 30, 2010, which claims benefit of priority to U.S. Provisional Patent Application Ser. No. 61/265,486, filed Dec. 1, 2009. The aforementioned applications are expressly incorporated herein by reference in their entirety and for all purposes.

TECHNICAL FIELD

This invention generally relates to cell biology and medicine. The invention provides compositions for making erythroid progenitor cells that comprise in vitro-activated bone marrow mesenchymal stem cells and embryoid bodies (EBs) or pluripotent stem cells, and methods for making and using them, including ameliorating (e.g., preventing or treating) anemia and/or stimulating erythropoiesis. In one embodiment, the invention provides methods of increasing propensity of committed stem cell differentiation towards the erythroid lineage.

BACKGROUND

Anemia can be treated by enhancing the production of or replacing or enhancing levels of red blood cells. Anemia may be chronic or acute. Chronic anemia may be caused by extrinsic red blood cell abnormalities, intrinsic abnormalities or impaired production of red blood cells. Extrinsic or extracorpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. Infections by parasites such as *Plasmodium*, chemical injuries from, for example, lead poisoning, and sequestration in the mononuclear system such as by hypersplenism can result in red blood cell disorders and deficiencies.

Generation of erythrocytes from embryonic stem (ES) cell-based approaches is limited by scalability and limited methodology for generating erythrocyte progenitors. Although previous technologies have used bone marrow and cord blood hematopoietic stem cells, useable production of erythroid progenitors has not been achieved. Conversely, technologies exist for terminal differentiation and enucleation of erythroid progenitors, however, production of ample amounts of the "starting cells" has not been successful.

SUMMARY

In alternative embodiments, the invention provides compositions and methods for generating or creating enhanced numbers of erythroid progenitor cells from embryonic stem cells, or equivalent cells. In one embodiment, the invention provides a new methodology that mimics the body's own processes for making red blood cells (RBCs). In alternative embodiments the compositions and methods of the invention are used to ameliorate anemia and/or stimulate erythropoiesis (e.g., stimulating red blood cell production or maturation) and erythropoietin (EPO) synthesis, e.g., an erythropoietin-alpha (EPO-α) synthesis. In another embodiment, the invention teaches methods of increasing propensity of committed stem cell differentiation towards the erythroid lineage.

In alternative embodiments, the invention provides compositions, products (articles) of manufacture, and/or isolates, mixtures or cultures of cells comprising: (1) in vitro-activated bone marrow mesenchymal stem cells (BM-MSC, also called a Marrow Stromal Cell, or MSC); (2) embryoid bodies (EBs) or pluripotent stem cells; and, (3) a sufficient amount of an erythropoietin (EPO), a composition or agent for stimulating an erythroid lineage commitment, or an equivalent thereof, to induce formation (or differentiation to) erythroid stem cells or erythroid progenitor cells, wherein the BM-MSC/MSC cells are activated by a method comprising (a) providing: (i) a bone marrow mesenchymal stem cell (BM-MSC) or a Marrow Stromal Cell; or, (ii) a bone marrow-derived cell that expresses (is positive for) the cell surface polypeptides CD105, CD166, CD29 and CD44, and does not express (is negative for) the cell surface polypeptides CD14, CD34 and CD45; and (b) culturing the cell of (a) under hypoxic conditions for at least about 6, 7, 8, 9, 10, 11, 12, 13, 14, 15, 16, 17, 18, 19, 20, 21, 22, 23, 24, 25 or 26 or more hours, or for between about 1 to 2 days.

In alternative embodiments of the compositions, products (articles) of manufacture, or isolates, mixtures or cultures of cells of the invention, culturing the cells of (a) under hypoxic conditions comprises culturing the cells under culture conditions comprising or equivalent to: (i) a maximum of between about 0.5% and 1%, or a maximum of between about 0.5% and 2% oxygen ($O_2$); (ii) about 0.1%, 0.2%, 0.3%, 0.4%, 0.5%, 0.6%, 0.7%, 0.8%, 0.9%, 1% or 2% oxygen ($O_2$): (iii) between about 0.1% and 2% oxygen ($O_2$); or, any of (i), (ii) or (iii) with 5% $CO_2$.

In alternative embodiments of the compositions, products of manufacture, or isolates, mixtures or cultures of cells of the invention, the cells of (a) comprise: (i) a bone marrow mesenchymal stem cell (BM-MSC)) or a Marrow Stromal Cell isolated from an individual or a human; or, (ii) a PROCHYMAL™ cell (Osiris Therapeutics, Inc. Columbia, Md.), or a POIETICS® cell (Lanza Cologne AG, Koeln, Germany).

In alternative embodiments: (a) the erythropoietin is a human erythropoietin, a recombinant erythropoietin, an isolated erythropoietin, an erythropoietin-alpha (EPO-α), an EPOGEN® (Epoetin.) (Amgen, Thousand Oaks, Calif.), a BETAPOIETIN™ (Cinnagen, Tehran, Iran) or any combination thereof; or, the erythropoietin is at a concentration of about 3 units/ml.; or (b) the composition or agent for stimulating an erythroid lineage commitment comprises an EPO mimetic; an EPO receptor (Epo-R) stimulating compound, e.g., an antibody that specifically binds to and stimulates the Epo-R, e.g., to mimic EPO as a ligand; an agent that activates biochemical pathways downstream of the EPO receptor, or any combination or equivalent thereof.

In alternative embodiments the compositions, products of manufacture, or isolates, mixtures or cultures of cells of the invention further comprise a matrices (matrix) resembling a bone marrow, a bone marrow microenvironment, or a decellularized matrices (matrix), or the isolate, mixture or culture of cells is contained or cultured in a bone marrow, a bone marrow microenvironment, or a decellularized matrices (matrix).

In alternative embodiments the compositions, products of manufacture, or isolates, mixtures or cultures of cells of the invention further comprise a lithium, a valproic acid, a sodium phenylbutyrate or a combination thereof.

In alternative embodiments the compositions, products of manufacture, or isolates, mixtures or cultures of cells of the invention further comprise a small molecule, a hormone or a cytokine that increases or upregulates erythropoiesis or red blood cell production in a mammal or a human.

In alternative embodiments, the invention provides methods for making erythroid progenitor cells comprising: (a) providing the composition, product of manufacture, or isolate, mixture or culture of cells of the invention; and (b) culturing or mixing the combination of in vitro-activated bone marrow mesenchymal stem cells (BM-MSC, or MSC); (2) embryoid bodies (EBs) or pluripotent stem cells; and, (3) a sufficient amount of erythropoietin or a composition or agent for stimulating an erythroid lineage commitment to induce formation (or differentiation to) erythroid stem cells or erythroid progenitor cells, for an amount of time sufficient to induce the formation of erythroid progenitor cells. The composition or agent for stimulating an erythroid lineage commitment can comprise an EPO mimetic; an EPO receptor (Epo-R) stimulating compound, e.g., an antibody that specifically binds to and stimulates the Epo-R, e.g., to mimic EPO as a ligand; an agent that activates biochemical pathways downstream of the EPO receptor, or any combination or equivalent thereof.

In alternative embodiments of the methods, the cells are cultured or mixed in a solution or media comprising an erythropoietin, and optionally the erythropoietin is a human erythropoietin, a recombinant erythropoietin, an isolated erythropoietin, an erythropoietin-alpha (EPO-α), an EPOGEN® (Epoetin-α) (Amgen, Thousand Oaks, Calif.), a BETAPOIETIN™ (Cinnagen, Tehran, Iran) or any combination thereof; and/or, the erythropoietin is at a concentration of about 3 units/ml in the solution or media.

In alternative embodiments of the methods, the cells are cultured or mixed in a matrices (matrix) resembling a bone marrow, a bone marrow microenvironment, or a decellularized matrices (matrix), or the isolate, mixture or culture of cells is contained or cultured in a bone marrow, a bone marrow microenvironment, or a decellularized matrices (matrix). The cells can be isolated, cultured and/or mixed in a media or a solution comprising (or consisting of) a lithium, a valproic acid, a sodium phenylbutyrate or a combination thereof.

In alternative embodiments of the methods, the cells are isolates, cultured and/or mixed in a media or a solution comprising a small molecule, a hormone or a cytokine that increases or upregulates erythropoiesis or red blood cell production in a mammal or a human. The cells can be derived from mammalian cells, e.g., the mammalian cells can be (or can be derived from) a human cell, a non-human primate cell, a monkey cell, a mouse cell, a rat cell, a guinea pig cell, a rabbit cell, a hamster cell, a goat cell, a bovine cell, an equine cell, an ovine cell, a canine cell or a feline cell.

The invention provides methods for increasing the propensity of a committed stem cell to differentiate towards an erythroid lineage comprising: (a) providing the composition, product of manufacture, or isolate, mixture or culture of cells of the invention; and (b) culturing or mixing the composition, product of manufacture, or isolate, mixture or culture of cells of (a) with a sufficient amount of erythropoietin to induce formation (or differentiation to) erythroid stem cells or erythroid progenitor cells, for an amount of time sufficient to induce the formation of erythroid progenitor cells.

The invention provides methods for increasing the propensity of a committed stem cell to differentiate towards an erythroid lineage comprising:

(1) providing an in vitro-activated bone marrow mesenchymal stem cells (BM-MSC, also called a Marrow Stromal Cell, or MSC), wherein the BM-MSC/MSC cells are activated by a method comprising (a) providing: (i) a bone marrow mesenchymal stem cell (BM-MSC) or a Marrow Stromal Cell; or, (ii) a bone marrow-derived cell that expresses (is positive for) the cell surface polypeptides CD105, CD166, CD29 and CD44, and does not express (is negative for) the cell surface polypeptides CD14, CD34 and CD45; and (b) culturing the cell of (a) under hypoxic conditions for at least about 6, 7, 8, 9, 10, 11, 12, 13, 14, 15, 16, 17, 18, 19, 20, 21, 22, 23, 24, 25 or 26 or more hours; and (2) culturing or mixing the in vitro-activated bone marrow mesenchymal stem cells with a sufficient amount of erythropoietin to induce formation (or differentiation to) erythroid stem cells or erythroid progenitor cells.

The invention provides kits comprising the compositions, products of manufacture, or isolates, mixtures or cultures of cells of the invention; and optionally further comprising instructions for practicing the method of the invention.

The invention provides uses of the compositions, products of manufacture, or isolates, mixtures or cultures of cells of the invention, to make erythroid progenitor cells.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

FIG. 1 illustrates a graph showing data from a flow cytometry experiment that demonstrated that the percentage of cells having a positive erythroid progenitor morphology is increased in cells cultured with hypoxia-treated BM-MSC, as discussed in Example 1, below.

Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

The invention provides compositions and methods for generating enhanced numbers of erythroid progenitor cells from embryonic stem cells. In alternative embodiments the compositions and methods of the invention are used to ameliorate anemia and/or stimulate erythropoiesis and EPO synthesis. While the invention is not limited by any particular mechanism of action, in one embodiment the invention provides methods and compositions capable of creating a microenvironment that resembles the natural hematopoietic environment in which erythroid-commitment occurs.

In alternative embodiments, the invention provides compositions, products of manufacture, isolates, mixtures and cultures of cells comprising in vitro-activated bone marrow mesenchymal stem cells (BM-MSC), also called Marrow Stromal Cells (MSCs), activated by hypoxic preconditioning, e.g., by culture in hypoxic conditions, e.g., by culture in the equivalent of between about 0.1% to 3% $O_2$ in cell culture. In alternative embodiments, the oxygen tension used for this in vitro-activation is similar to the physiologic niche for mesenchymal stem cells (MSC) such as bone marrow mesenchymal stem cells (BM-MSC) in an in vivo bone marrow environment, e.g., at between about 2% to 7% $O_2$.

In alternative embodiments, the invention utilizes compositions and methods that replicate a bone marrow microenvironment by addition of hone marrow mesenchymal stem cells (BM-MSC) and stimulate production of therapeutic factors by temporary induction of hypoxia in the bone marrow mesenchymal stem cells at a level that does not substantially decrease viability, followed by co-culturing with an embryoid body or equivalent. In practicing this invention, in one embodiment EPO is added; embryoid bodies are more erythropoietic when EPO is added with the hypoxic BM-MSC; however in alternative embodiments alternative compositions or means for stimulating erythroid commitment may be substituted, for example: by using EPO mimetics, EPO-receptor stimulating compounds, and/or agents that stimulate biochemical pathways downstream of the EPO receptor.

In alternative embodiments, the invention provides for scalable generation of erythrocytes using embryonic stem cell cultures in e.g., biosimilar matrices and the like. This invention can generate superior amounts of erythroid progenitors which are useful for terminal differentiation and scalable red blood cell production. In alternative embodiments, the invention uses various "activated" stromal cell populations as part of a co-culture mixture to augment formation of (or differentiation to) erythroid stem cells or erythroid progenitor cells, and thus augment erythropoiesis. In alternative embodiments, the invention provides for upregulation of erythropoiesis by culture of cells (including embryoid bodies (EBs) and/or pluripotent stem cells) in matrices resembling hone marrow, such as decellularized matrices, to augment this process.

In alternative embodiments, lithium, valproic acid, sodium phenylbutyrate to expand progenitors is also used to practice the invention.

Kits and Instructions

The invention provides kits comprising compositions and methods of the invention, including instructions for use thereof. In alternative embodiments, the invention provides kits comprising a composition, product of manufacture, or isolates, mixture or culture of cells of the invention; wherein optionally the kit further comprises instructions for practicing a method of the invention.

Diagnosing and Treating Anemia

In alternative embodiments, compositions, products of manufacture, and/or isolates, mixtures or cultures of cells of the invention, and methods of the invention, are used to induce formation of (or differentiation to) erythroid stem cells or erythroid progenitor cells from progenitor cells (such as embryoid bodies (EBs) or pluripotent stem cells). In one embodiment, the methods of the invention further comprise inducing and/or differentiating erythroid progenitor cells to differentiate to red blood cells. Thus, the compositions, products of manufacture, and/or isolates, mixtures or cultures of cells of the invention are used to ameliorate or prevent an anemia, and/or to stimulate erythropoiesis in an individual such as a human.

In practicing the invention any diagnostic method for determining when anemia is present, or the severity of the anemia, or whether the anemia is responding to treatment e.g., responding to administration of RBCs generated by compositions and/or methods of this invention. For example, because alternative embodiments of the invention encompass ameliorating or preventing anemia caused by a genetic disorder, an infection, a dietary disorder or deficiency, a pollutant, a pesticide, herbicide or insecticide, a poison, a venom, a toxin, a biological agent, a drug, a cancer or a cancer therapeutic or cancer therapy, the presence of any of these conditions can be used as a basis for diagnosing or predicting the possible onset of anemia, and any diagnostic technique related to any of these conditions, treatments, infections or exposures can be used.

Because alternative embodiments of the invention encompass ameliorating or preventing anemia caused by a drug-induced anemia; caused by an infection; caused by an iron deficiency; caused by rhesus disease (hemolytic disease of newborn); caused by sickle-cell disease, thalassemia or Plummer-Vinson syndrome (PVS); a sideroblastic anemia-congenital or acquired; caused by Gaucher's disease; caused by a vitamin deficiency; caused by autoimmune hemolytic anemia (AIHA); caused by a cancer; or, caused by heavy metal poisoning or pyridoxine deficiency, any diagnostic test for any of these conditions, treatments, infections or exposures can be used.

In alternative embodiments, in practicing compositions and/or methods of this invention, anemia can be diagnosed and/or managed using complete blood counts, the number of red blood cells and/or the hemoglobin level. Automatic counters that measure the size of the red blood cells, e.g., by flow cytometry, can be used to distinguish between the causes of anemia; noting that in alternative embodiments the compositions and methods of the invention are used to ameliorate or prevent microcytic, normocytic or macrocytic forms of anemia. Examination of a stained blood smears, e.g., using a microscope, also can be used. In alternative embodiments, four parameters are used to diagnose or assess anemia: RBC count, hemoglobin concentration, mean corpuscular volume (MCV) and red blood cell distribution width (RDW); e.g., to assess the individual's response to administration of a chimeric protein of the invention, or administration of a nucleic acid encoding a chimeric protein of the invention. Hematocrit, mean corpuscular hemoglobin (or "mean cell hemoglobin", MCH), and mean corpuscular hemoglobin concentration (or MCHC) also can be calculated, and compared to values adjusted for age and sex. For example, for adult men a hemoglobin level less than 13.0 g/dl (grams per deciliter) is diagnostic of anemia, and for adult women, the diagnostic threshold is below 12.0 g/dl. A normal hematocrit value is 32 to 36 g/dl.

In alternative embodiments, other tests also can be used, e.g., the erythrocyte sedimentation rate (ESR); the reticulocyte production index (RPI, also called a corrected reticulocyte count); folic acid, serum iron, hepcidin, transferrin, vitamin B12 and/or creatinine levels; e.g., to assess the individual's response to administration of a chimeric protein of the invention, or administration of a nucleic acid encoding a chimeric protein of the invention.

In alternative embodiments, methods of this invention can be practiced with other treatments for anemia, e.g., blood transfusions, hyperbaric medicine, administration of an EPO to a patient, e.g., a recombinant erythropoietin; for example, any form of erythropoietin can be used, including epoetin (e.g., EPOGEN™, PROCRIT™, EPREX™, NEORECORMON™) (Amgen, Thousand Oaks, Calif.), or darbepoetin, a synthetic form of EPO (e.g., ARANESP™) (Amgen, Thousand Oaks, Calif.). In alternative embodiments, methods of this invention can be practiced with other treatments for anemia such as administering a VEGF antagonist, as described e.g., in U.S. Pat. No. 7,351,411; administering a hyperglycosylated analog of EPO, as described e.g., in U.S. Pat. No. 7,304,150 or U.S. Pat. No. 7,262,166.

Individuals that can benefit by practicing the compositions and methods of this invention, e.g., that can benefit (e.g., by treating, ameliorating and/or preventing) from an increase in levels of erythroid stem cells or erythroid progenitor cells, and/or increases in RBC levels, include humans or animals, include e.g., individuals with a peripheral nerve injury; a hemoglobin H disease; a testicular torsion-detorsion; post-infarct myocardial damage; or a neurologic disorder; or when an increase in endogenous EPO levels would act as a neuroprotective, e.g., in low birth weight infants. In alternative embodiments, the neurologic disorder is ischemic stroke, intracerebral hemorrhage, subarachnoid hemorrhage, traumatic brain injury or Parkinson's disease.

Wounds and inflammations also can be treated or ameliorated by practicing the compositions and methods of this invention, e.g., including humans or animals. In alternative embodiments, wounds and inflammations that can benefit from an increase in levels of erythroid stem cells or erythroid progenitor cells, and/or increases in RBC levels, by practicing the compositions and methods of this invention include conjunctivitis; surgical or accidental wounds; a bedsore; a burn; an inflammation of the skin, mucous membranes, airways or lungs; an eczema or a skin disorder accompanied by necrosis, by dermatitis, by psoriasis or by diabetes mellitus. The pharmaceutical formulation applied can be a topical application, e.g., in the form of an ointment, a cream, a powder, an emulsion, a gel, a glycerogelatin, a paste, a plaster, a sprayable composition or a lotion.

The methods of the invention can further comprise co-administration with other drugs or pharmaceuticals, e.g., compositions for treating anemia and related symptoms or conditions. For example, the methods and/or compositions and formulations of the invention can be co-formulated with and/or co-administered with antibiotics (e.g., antibacterial or bacteriostatic peptides or proteins), including those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Products of Manufacture, Implants and Artificial Organs

The invention also provides implants and artificial organs, bioreactor systems, cell culture systems, plates, dishes, tubes, bottles and flasks and the like comprising compositions, products of manufacture, or isolates, mixtures or cultures of cells of this invention. Any implant, artificial organ, bioreactor systems, cell culture system, cell culture plate, dish (e.g., petri dish), cell culture tube and/or cell culture flask (e.g., a roller bottle) can be used to practice this invention.

In alternative embodiments the invention provides a bioreactor, implant, stent, artificial organ or similar device comprising compositions, products of manufacture, or isolates, mixtures or cultures of cells of this invention; for example, including implants as described in U.S. Pat. Nos. 7,388,042; 7,381,418; 7,379,765; 7,361,332; 7,351,423; 6,886,568; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

The invention will be further described with reference to the following examples; however, it is to be understood that the invention is not limited to such examples.

EXAMPLES

Example 1

Compositions and Methods of the Invention are Effective in the Amelioration of Anemia The data presented herein demonstrates that the compositions and methods of the invention are effective in enhancing generation of erythroid progenitors.

hES Cell Culture and Differentiation hES cell line H9 (WiCell Research Institute (WI, USA) was cultured on a feeder layer of mouse embryonic fibroblasts (MEFs, Global Stem Cell Technologies, USA) in the culture medium consisting of DMEM-F12 with Knockout Serum Replacement (20%), L-Glutamine (0.8 mM), 2-Mercaptoethanol (119 µM), Non-Essential Amino Acid Solution (1%), and human recombinant bFGF (10 ng/ml) (all from Invitrogen, CA, USA) in standard cell culture condition (37° C., 5% $CO_2$) and split every 3rd day.

Embryoid Body Formation

When the hES culture reached 75% confluence, cells were used for creation of embryoid body (EB). The hES cells have been detached by mechanical means and small clumps of cells were resuspended in serum-free STEMLINE II™ Hematopoietic Stem Cell Expansion Medium (Sigma) containing BMP-4 and VEGF (50 ng/ml of each) (Invitrogen, CA, US). After 48 hours of incubation, half of the culture media was replaced with the STEMLINE II™ media containing BMP-4 and VEGF (both at 50 ng/ml), SCF, Tpo, and FLT3 ligand (all at 40 ng/ml) (Invitrogen, CA, US). Half of the medium was replaced every 48 hours with fresh medium containing BMP-4, VEGF, SCF, Tpo, and FLT3 ligand at concentrations described above. In the majority of experiments, EBs were collected after 72 hours of culture and dispersed to single cell suspension by incubation with Trypsin (0.05%) and EDTA (Invitrogen), and passing through 22 G needle and 40 µm cell strainer. Single cells were resuspended in Stemline II medium and added to the activated stromal cells as indicated in the coculture section.

Activation of MSC Stromal Cells

BM-MSC (Lonza, Walkersville Md.) The POIETICS® Human Mesenchymal Stem Cells provided by Lonza are similar to Osiris's PROCHYMAL™ product which is currently in Phase III trials. Cells are maintained in Mesenchymal Stem Cell Basal Medium (MSCBM) and passaged every 3-4 days as recommended by the manufacturer. Cells are positive (>90%) for CD105, CD166, CD29, and CD44. Cells test negative (<5%) for CD14, CD34 and CD45. Cells are used before beyond passage 5. Differentiation ability to ensure mesenchymal stem cell identity was tested by treatment with adipogenic, chondrogenic, and osteogenic induction media as described by us.

Preparation of Plate BM-MSC were washed once with phosphate buffered saline (PBS) and de-adhered by 0.05% trypsin/EDTA (Invitrogen) at 37° C. for 10 min. Cells were then washed again and plated in 6 well plates at a density of 50,000 BM-MSC per well. Each well of the 6-well plate contained 3 ml of alpha-MEM supplemented with 15% umbilical cord blood serum, 1 mM glutamine, 1% nonessential amino acid. After 24 hours, the surface of the wells was washed with PBS to remove non-adherent cells.

Treatment of Plate: BM-MSC were exposed to 0.5% oxygen ($O_2$) conditions for 24 hours. Briefly, confluent cells were split 1:2 and once contluency is reached, fresh media was added and cells were placed in a PRO-OX-C™ chamber system (Biospherix, Redfield, N.Y.) for 24 hours. Cells where cultured in 0.5% $O_2$, 5% $CO_2$, and the remainder nitrogen under fully humidified conditions (11). Cellular viability was >95% before experimental use. Cells were subsequently irradiated (25 Gy). Cultures were performed in 3 ml of alpha-MEM supplemented with 15% umbilical cord blood serum, 1 mM glutamine, 1% nonessential amino acid.

Coculture with Embryoid Bodies: Embryoid bodies derived single cell suspensions were lifted from ES cell cultures using a pipette and about $10^4$ cells per well (3 ml volume) within the 6 well plate as described above. At various timepoints in culture cell layers were dissociated by 0.05% trypsin/EDTA and assessed for marker expression by flow cytometry or for colony forming activity. The alpha-MEM media described above was used, with addition of 3 units/mL erythropoietin.

Flow cytometry: Harvested adherent cells were preincubated with rabbit serum to block nonspecific binding and subsequently stained with mAbs conjugated to FITC, phycocrythrin (PE), or allophycocyanin (APC). Stained cells were washed with PBS and analyzed by using a FACS CALIBUR™ flow cytometer system (BD Biosciences). Propidium iodide (PI)-stained cells were gated out to exclude dead cells. mAbs against human CD45 (DakoCytomation), GPA (BD Pharmingen), CD71 (Beckman Coulter), and CD81 (BD).

Results: FIG. 1 graphically illustrates the percentage of cells positive erythroid progenitor morphology is increased in the cells cultured with hypoxia-treated BM-MSC.

FIG. 1: Increased Percentage of Erythroid Blast Progenitors:
1. column labeled #1 (the left column)=No Feeder
2. column labeled #2=Fibroblast Feeder
3. column labeled #3 BM-MSC=Normoxic
4. column labeled #4 BM-MSC=Hypoxic A number of embodiments of the invention have been described. Nevertheless, it will be understood that various modifications may be made without departing from the spirit and scope of the invention. Accordingly, other embodiments are within the scope of the following claims.

What is claimed is:

1. A composition, a product or an article of manufacture, or an isolate, a mixture or a culture of human cells, for producing human erythroid stem cells or human erythroid progenitor cells for in vivo applications, comprising:
   (1) in vitro-activated human bone marrow mesenchymal stem cells (BM-MSC, MSC);
   (2) human embryoid bodies (EBs) or human pluripotent stem cells; and,
   (3) a sufficient amount of a human erythropoietin to induce formation or differentiation to human erythroid stem cells or human erythroid progenitor cells,
   wherein the human BM-MSC/MSC cells are activated by a method comprising
   (a) providing:
      (i) a human bone marrow mesenchymal stem cell (BM-MSC) or a human Marrow Stromal Cell; or,
      (ii) a human bone marrow-derived cell that expresses or is positive for a the cell surface polypeptides CD105, CD166, CD29 and CD44, and does not express or is negative for the cell surface polypeptides CD14, CD34 and CD45; and
   (b) culturing the cell of (a) under hypoxic conditions for at least about 6 or more hours, or between 1 to 2 days.

2. The composition, product of manufacture, or isolate, mixture or culture of cells of claim 1, wherein culturing the cells of (a) under hypoxic conditions comprises culturing the cells under culture conditions comprising or equivalent to:
   (i) a maximum of between about 0.5% and 1%, or a maximum of between about 0.5% and 2% oxygen ($O_2$);
   (ii) about 0.1%, 0.2%, 0.3%, 0.4%, 0.5%, 0.6%, 0.7%, 0.8%, 0.9%, 1% or 2% oxygen ($O_2$);
   (iii) between about 0.1% and 2% oxygen ($O_2$); or,
   (iv) any of (i), (ii) or (iii) with 5% $CO_2$.

3. The composition, a product or an article of manufacture, or an isolate, a mixture or a culture of cells of claim 1, wherein the cell of (a) comprise a human bone marrow mesenchymal stem cell (BM-MSC) or a human Marrow Stromal Cell isolated from an individual or a human.

4. The composition, a product or an article of manufacture, or an isolate, a mixture or a culture of cells of claim 1, wherein the erythropoietin is an isolated human erythropoietin.

5. The composition, product of manufacture, or isolate, mixture or culture of cells of claim 1, further comprising a matrices (matrix) resembling a bone marrow, a bone marrow microenvironment, or a decellularized matrices (matrix), or the mixture or culture of cells is contained or cultured in a bone marrow, a bone marrow microenvironment, or a decellularized matrices (matrix).

6. The composition, product of manufacture, or isolate, mixture or culture of cells of claim 1, further comprising a lithium, a valproic acid, a sodium phenylbutyrate or a combination thereof.

7. The composition, product of manufacture, or mixture or culture of cells of claim 1, further comprising a small molecule, a hormone or a cytokine that increases or upregulates erythropoiesis or red blood cell production in a mammal or a human.

8. A kit comprising the composition, product of manufacture, or isolate, mixture or culture of cells of claim 1.

9. The kit of claim 8, further comprising instructions for using the composition, product of manufacture, isolate, mixture or culture of cells of claim 1.

10. The composition, product or article of manufacture, or the isolate or mixture or culture of cells, of claim 1, wherein in step (b) the cell of (a) is cultured under hypoxic conditions for at least about 7, 8, 9, 10, 11, 12, 13, 14, 15, 16, 17, 18, 19, 20, 21, 22, 23, 24, 25 or 26 or more hours.

11. The composition, product of manufacture, or isolate, mixture or culture of cells of claim 1, wherein the erythropoietin is at a concentration of about 3 units/ml.

12. The composition, product or article of manufacture, or the isolate or mixture or culture of cells, of claim 1, wherein in step (b) the cell of (a) is cultured under hypoxic conditions for between about 6 hours to 2 days.

13. The composition, product or article of manufacture, or the isolate or mixture or culture of cells, of claim 12, wherein in step (b) the cell of (a) is cultured under hypoxic conditions for between about 6 to 26 hours.

14. The composition, product or article of manufacture, or the isolate or mixture or culture of cells, of claim 1, wherein the in vitro-activated human bone marrow mesenchymal stem cells (BM-MSC, MSC) are adherent cells, or are adherent to a solid surface or a plate surface.

15. The composition, a product or an article of manufacture, or an isolate, a mixture or a culture of cells of claim 1, wherein the in-vitro activated human bone marrow mesenchymal stem cells (BM-MSC, MSC) are irradiated but are greater than about 95% viable when mixed or co-cultured with the human embryoid bodies (EBs) or human pluripotent stem cells.

16. A composition, a product or an article of manufacture, or an isolate, a mixture or a culture of human cells, comprising:
(1) in vitro-activated human bone marrow mesenchymal stem cells (BM-MSC, MSC);
(2) human embryoid bodies (EBs) or pluripotent human stem cells; and,
(3) a sufficient amount of a human erythropoietin to induce formation or differentiation to human erythroid stem cells or human erythroid progenitor cells,
wherein the human BM-MSC/MSC cells are activated by a method comprising
(a) providing:
(i) a human bone marrow mesenchymal stem cell (BM-MSC) or a human Marrow Stromal Cell; or,
(ii) a human bone marrow-derived cell that expresses or is positive for a the cell surface polypeptides CD105, CD166, CD29 and CD44, and does not express or is negative for the cell surface polypeptides CD14, CD34 and CD45; and
(b) culturing the cell of (a) under hypoxic conditions for at least about 6 or more hours, or between 1 to 2 days.

17. The composition, product or article of manufacture, or the isolate or mixture or culture of cells of claim 16, wherein in step (b) the cell of (a) is cultured under hypoxic conditions for between about 6 hours to 2 days.

18. The composition, product or article of manufacture, or the isolate or mixture or culture of cells of claim 16, wherein in step (b) the cell of (a) is cultured under hypoxic conditions for between about 6 hours to 26 hours.

* * * * *